United States Patent
Song et al.

(10) Patent No.: US 9,367,664 B2
(45) Date of Patent: Jun. 14, 2016

(54) MOBILE APPARATUS FOR EXECUTING SENSING FLOW FOR MOBILE CONTEXT MONITORING, METHOD OF EXECUTING SENSING FLOW USING THE SAME, METHOD OF CONTEXT MONITORING USING THE SAME AND CONTEXT MONITORING SYSTEM INCLUDING THE SAME

(71) Applicant: Korea Advanced Institute of Science and Technology, Daejeon (KR)

(72) Inventors: June-Hwa Song, Daejeon (KR);
Young-Hyun Ju, Daejeon (KR);
Chul-Hong Min, Daejeon (KR);
Young-Ki Lee, Daejeon (KR); Ji-Hyun Yu, Daejeon (KR); In-Sik Shin, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 255 days.

(21) Appl. No.: 14/073,217

(22) Filed: Nov. 6, 2013

(65) Prior Publication Data
US 2015/0106817 A1    Apr. 16, 2015

(30) Foreign Application Priority Data
Oct. 11, 2013  (KR) .................. 10-2013-0121233

(51) Int. Cl.
| | | |
|---|---|---|
| G01D 3/00 | (2006.01) | |
| G06F 19/00 | (2011.01) | |
| G06F 9/48 | (2006.01) | |
| G06F 11/30 | (2006.01) | |
| G06F 11/34 | (2006.01) | |
| H04W 4/00 | (2009.01) | |
| G06N 7/00 | (2006.01) | |

(52) U.S. Cl.
CPC .......... *G06F 19/3406* (2013.01); *G06F 9/4881* (2013.01); *G06F 11/3058* (2013.01); *G06F 11/3096* (2013.01); *G06F 11/3409* (2013.01); *G06N 7/005* (2013.01); *H04W 4/006* (2013.01)

(58) Field of Classification Search
USPC ............. 702/108; 370/231, 252, 328; 706/46; 718/102, 100; 709/235
See application file for complete search history.

(56) References Cited

U.S. PATENT DOCUMENTS

| | | | | |
|---|---|---|---|---|
| 8,565,109 | B1 * | 10/2013 | Poovendran | .......... H04W 4/006 370/231 |
| 2008/0235172 | A1 * | 9/2008 | Rosenstein | ............ G06N 7/005 706/46 |
| 2012/0203491 | A1 * | 8/2012 | Sun | ..................... G06F 19/3406 702/108 |

* cited by examiner

*Primary Examiner* — Kyung H Shin
(74) *Attorney, Agent, or Firm* — Womble Carlyle Sandridge & Rice, LLP (57) ABSTRACT

A mobile apparatus includes a sensing handler and a processing handler. The sensing handler includes a plurality of sensing operators. The sensing operator senses data during a sensing time corresponding to a size of C-FRAME and stops sensing during a skip time. The C-FRAME is a sequence of the sensed data to produce a context monitoring result. The processing handler includes a plurality of processing operators. The processing operator executes the sensed data of the sensing operator in a unit of F-FRAME. The F-FRAME is a sequence of the sensed data to execute a feature extraction operation.

26 Claims, 10 Drawing Sheets

MOBILE APPARATUS FOR EXECUTING SENSING FLOW FOR MOBILE CONTEXT MONITORING, METHOD OF EXECUTING SENSING FLOW USING THE SAME, METHOD OF CONTEXT MONITORING USING THE SAME AND CONTEXT MONITORING SYSTEM INCLUDING THE SAME

PRIORITY STATEMENT

This application claims priority under 35 U.S.C. §119 to Korean Patent Application No. 10-2013-0121233, filed on Oct. 11, 2013 in the Korean Intellectual Property Office (KIPO), the contents of which are herein incorporated by reference in their entireties.

BACKGROUND

1. Technical Field

Example embodiments relate to a mobile apparatus, a method of executing a sensing flow using the mobile apparatus, a method of context monitoring using the mobile apparatus and a context monitoring system having the mobile apparatus. More particularly, example embodiments relate to a mobile apparatus capable of improving utility of application by coordinating resource uses of concurrent executing applications, a method of executing a sensing flow using the mobile apparatus, a method of context monitoring using the mobile apparatus and a context monitoring system having the mobile apparatus.

2. Description of the Related Art

Recent paradigm of information communication technology may be a ubiquitous computing, a ubiquitous network, a pervasive computing and so on. "Ubiquitous" means that a user may easily get any desired information anytime and anywhere. In an upcoming ubiquitous age, smart objects, having computing and communication function, may recognize a dynamic environment and be adaptive to the dynamic environment. In other words, the smart objects may have a context awareness feature.

A personal area network (PAN) is one of the core technologies realizing the ubiquitous network having the context awareness feature. The PAN is a network which is provided to a person to communicate in a close range. The person using the PAN may be connected with various devices in about 10 m with respect to the person.

The PAN is suitable for a context monitoring application, which provides proper services in response to an action of the user, a status of the user and an environment around the user. In the PAN environment, the network is operated around the person so that a portable mobile apparatus, capable of receiving data from various sensors and outputting context information to the context monitoring applications, may be a core platform. For example, a mobile terminal may recognize a context of the user by collecting and transmitting the sensed data, and may provide information to the context monitoring application by analyzing the sensed data. The context monitoring application may provide proper services to the user according to the context of the user. Accordingly, the mobile apparatus capable of supporting a number of the context monitoring applications may be necessary.

Emerging continuous mobile sensing applications may significantly change workload patterns imposed on the mobile apparatus. Going beyond the confines of typical user-interactive mobile applications such as web browsers and games, the user-interactive mobile applications continuously run in the background and provide autonomous, situation-aware services without a user's intervention. Such concurrent workloads will raise an unprecedented challenge, incurring severe resource contention on the resource-scarce mobile apparatus. The contention is aggravated due to the continuous heavy CPU consumption of individual sensing applications to process high-rate sensor data. More important, such sensing and processing workloads may be handled near real-time to provide timely services. Even worse, the total resource availability might be limited further, deteriorating the contention; user's may not exhaust the whole CPU cycles and battery only for background applications. Under such contentious situation, greedy resource use by an application may result in serious degradation of service qualities of the other applications. The performance of other daily use of the mobile apparatus may be also degraded.

SUMMARY

Example embodiments provide a mobile apparatus improving utility of application by coordinating resource uses of concurrent executing applications.

Example embodiments also provide a method of executing a sensing flow using the mobile apparatus.

Example embodiments also provide a method of monitoring a context using the mobile apparatus.

Example embodiments also provide a context monitoring system having the mobile apparatus.

In an example mobile apparatus according to the present inventive concept, the mobile apparatus includes a sensing handler and a processing handler. The sensing handler includes a plurality of sensing operators. The sensing operator senses data during a sensing time corresponding to a size of C-FRAME and stops sensing during a skip time. The C-FRAME is a sequence of the sensed data to produce a context monitoring result. The processing handler includes a plurality of processing operators. The processing operator executes the sensed data of the sensing operator in a unit of F-FRAME. The F-FRAME is a sequence of the sensed data to execute a feature extraction operation.

In an example embodiment, the C-FRAME may include a plurality of the F-FRAMEs.

In an example embodiment, the mobile apparatus may further include a flow analyzer receiving information for a sensing flow from an application and determining a size of the C-FRAME of the sensing flow and a size of the F-FRAME of the sensing flow.

In an example embodiment, the flow analyzer may receive a necessary monitoring interval and a monitoring delay from the application. The necessary monitoring interval may represent how often the application needs to monitor a user's situation. The monitoring delay may represent time taken to generate the context monitoring result from a moment that a final F-FRAME in the C-FRAME is ready.

In an example embodiment, the mobile apparatus may further include a flow execution planner determining a monitoring interval of the C-FRAME based on the size of the C-FRAME, the size of the F-FRAME and the necessary monitoring interval and outputting the monitoring interval of the C-FRAME to the sensing handler. The monitoring interval of the C-FRAME of the sensing flow may be substantially equal to a sum of the sensing time and the skip time.

In an example embodiment, the mobile apparatus may further include a resource monitor determining a CPU availability of the mobile apparatus and outputting the CPU availability to the flow execution planner. The flow execution planner may determine the monitoring interval of the C-FRAME of the sensing flow based on the size of the C-FRAME, the size of the F-FRAME, the necessary monitoring interval and the CPU availability.

In an example embodiment, the necessary monitoring interval may have a type of utility function, the utility function having utility values of the application according to the monitoring intervals.

In an example embodiment, when the monitoring interval of a plurality of sensing flows is pi and the utility function of the sensing flows is ui, the flow execution planner may determine the monitoring interval as a formula, maximize $\Sigma ui(pi)$.

In an example embodiment, when cti is a CPU time required to process the C-FRAME of a flow, FLOWi and 1−CPUf is a CPU availability for the applications, the flow execution planner may determine the monitoring interval under a constraint of $\Sigma cti/pi \leq 1-CPUf$.

In an example embodiment, when eci is energy required to process the C-FRAME of a flow, FLOWi and Elimit is an energy availability for the applications, the flow execution planner may determine the monitoring interval under a constraint of $\Sigma eci/pi \leq Elimit$.

In an example embodiment, the sensing flows may include respective F-FRAME queues. The mobile apparatus may further include a flow scheduler determining an execution order of the F-FRAMEs by selecting a F-FRAME queue among the F-FRAME queues.

In an example embodiment, the flow scheduler may determine the execution order of the F-FRAMEs based on the monitoring delay.

In an example embodiment, a function of satisfy(ci) represents 1 if a context monitoring result for i-th flow, FLOWi is generated by processing the F-FRAMEs in the F-FRAME queue in the monitoring delay and represents 0. The flow scheduler determines the execution order of the F-FRAMEs using a formula, max imize$\Sigma$satisfy(ci).

In an example embodiment, a j-th F-FRAME of an i-th C-FRAME (C-FRAMEi) is F-FRAMEi,j, di is a tolerable delay of the FLOWi, ri,j is a remaining time to collect the remaining F-FRAMEs in the C-FRAMEi, epti,j is an expected time to process the unprocessed F-FRAMEs in the C-FRAMEi and a slack time of the F-FRAMEi,j is determined as a formula, slacktime(F-FRAMEi,j)=di+ri, j-epti, j. The flow scheduler may select the F-FRAME having a least slack time.

In an example embodiment, the mobile apparatus may further include a CPU scheduler outputting a CPU quota to the flow execution planner.

In an example method of executing a sensing flow according to the present inventive concept, the method includes sensing data during a sensing time corresponding to a size of C-FRAME and stopping sensing during a skip time using a plurality of sensing operators and executing the sensed data of the sensing operator in a unit of F-FRAME using a processing operator. The C-FRAME is a sequence of the sensed data to produce a context monitoring result. The F-FRAME is a sequence of the sensed data to execute a feature extraction operation.

In an example embodiment, the C-FRAME may include a plurality of the F-FRAMES.

In an example embodiment, the method may further include receiving information for a sensing flow from an application and determining a size of the C-FRAME of the sensing flow and a size of the F-FRAME of the sensing flow.

In an example embodiment, the method may further include receiving a necessary monitoring interval and a monitoring delay from the application. The necessary monitoring interval may represent how often the application needs to monitor a user's situation. The monitoring delay may represent time taken to generate the context monitoring result from a moment that a final F-FRAME in the C-FRAME is ready.

In an example embodiment, the method may further include determining a monitoring interval of the C-FRAME based on the size of the C-FRAME, the size of the F-FRAME and the necessary monitoring interval. The monitoring interval of the C-FRAME of the sensing flow may be substantially equal to a sum of the sensing time and the skip time.

In an example embodiment, the method may further include determining a CPU availability of the mobile apparatus. The monitoring interval of the C-FRAME of the sensing flow may be determined based on the size of the C-FRAME, the size of the F-FRAME, the necessary monitoring interval and the CPU availability.

In an example embodiment, the necessary monitoring interval may have a type of utility function, the utility function having utility values of the application according to the monitoring intervals.

In an example embodiment, the sensing flows may include respective F-FRAME queues. The method may further include determining an execution order of the F-FRAMEs by selecting a F-FRAME queue among the F-FRAME queues.

In an example embodiment, the execution order of the F-FRAMEs, may be determined based on the monitoring delay.

In an example method of monitoring a context according to the present inventive concept, the method includes receiving a context monitoring request from an application, sensing data during a sensing time corresponding to a size of C-FRAME and stopping sensing during a skip time using a plurality of sensing operators based on the context monitoring request, executing the sensed data of the sensing operator in a unit of F-FRAME using a processing operator based on the context monitoring request and outputting the context monitoring result to the application. The C-FRAME is a sequence of the sensed data to produce a context monitoring result. The F-FRAME is a sequence of the sensed data to execute a feature extraction operation.

In an example context monitoring system according to the present inventive concept, the context monitoring system includes a sensor, a mobile apparatus and an application. The sensor generates sensed data. The mobile apparatus includes a sensing handler and a processing handler. The sensing handler includes a plurality of sensing operators. The sensing operator senses data during a sensing time corresponding to a size of C-FRAME and stops sensing during a skip time. The C-FRAME is a sequence of the sensed data to produce a context monitoring result. The processing handler includes a plurality of processing operators. The processing operator executes the sensed data of the sensing operator in a unit of F-FRAME. The F-FRAME is a sequence of the sensed data to execute a feature extraction operation. The application receives the context monitoring result from the mobile apparatus.

According to the mobile apparatus, the method of executing the sensing flow, the method of monitoring the context, and the context monitoring system, contentious concurrent workloads of the applications may be coordinated on the whole so that potential imbalances in the service qualities of applications may be effectively resolved. In addition, developer may easily build sensing applications without concerning severe resource contention and the dynamics caused by concurrent applications. Thus, the resource uses of the contentious concurrent applications are coordinated so that the utility of the application may be maximized.

BRIEF DESCRIPTION OF THE DRAWINGS

The above and other features and advantages of the present inventive concept will become more apparent by describing in detailed example embodiments thereof with reference to the accompanying drawings, in which.

DETAILED DESCRIPTION OF THE EMBODIMENTS

The present inventive concept now will be described more fully hereinafter with reference to the accompanying drawings, in which exemplary embodiments of the present invention are shown. The present inventive concept may, however, be embodied in many different forms and should not be construed as limited to the exemplary embodiments set fourth herein.

Rather, these exemplary embodiments are provided so that this disclosure will be thorough and complete, and will fully convey the scope of the present invention to those skilled in the art. Like reference numerals refer to like elements throughout.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, the present inventive concept will be explained in detail with reference to the accompanying drawings.

Figure 1:
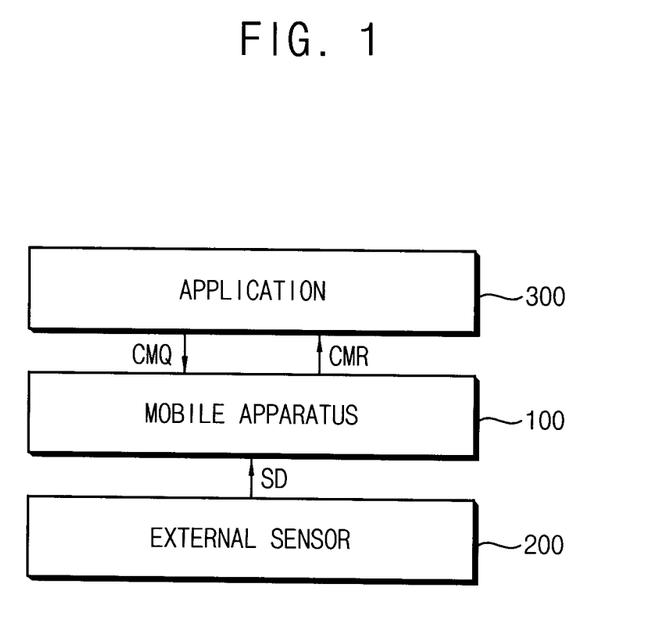
FIG. 1 is a block diagram illustrating a context monitoring system according to an example embodiment of the present inventive concept.

FIG. 1 is a block diagram illustrating a context monitoring system according to an example embodiment of the present inventive concept.

Referring to FIG. 1, the context monitoring system includes a mobile apparatus 100, an external sensor 200 and a context monitoring application 300.

The mobile apparatus 100 receives a context monitoring request (CMQ) from the context monitoring application 300 operating a context monitoring function. The mobile apparatus 100 receives sensed data SD from the external sensor 200. The mobile apparatus 100 determines context monitoring result CMR. The mobile apparatus 100 outputs the context monitoring result CMR to the application 300. A structure of the mobile apparatus 100 is explained in detail referring to FIG. 2.

The external sensor 200 provides the sensed data SD to the mobile apparatus 100. Alternatively, the external sensor 200 may provide feature data extracted from the sensed data SD to the mobile apparatus 100.

For example, the external sensor 200 may include a plurality of sensors. The external sensor 200 may be a light sensor, a temperature sensor, a position sensor, a dust sensor, an ultraviolet ray sensor, a hygrometer, a carbon dioxide detector, an ambient sound detector, an accelerometer and so on. Accordingly, the external sensor 200 may detect light, temperature, position, dust quantity, ultraviolet ray quantity, humidity, carbon dioxide quantity, ambient sound, acceleration and so on. The external sensor 200 may be a wearable sensor attached to a human body who is a user of the mobile apparatus 100.

The sensed data SD from the external sensor 200 are provided to the mobile apparatus 100, and are used to determine whether the sensed data SD satisfies a context requested by the context monitoring application 300.

The context monitoring application 300 requests the CMQ according to an object of program to the mobile apparatus 100. The context monitoring application 300 receives the context monitoring result CMR from the mobile apparatus 100.

Figure 2:
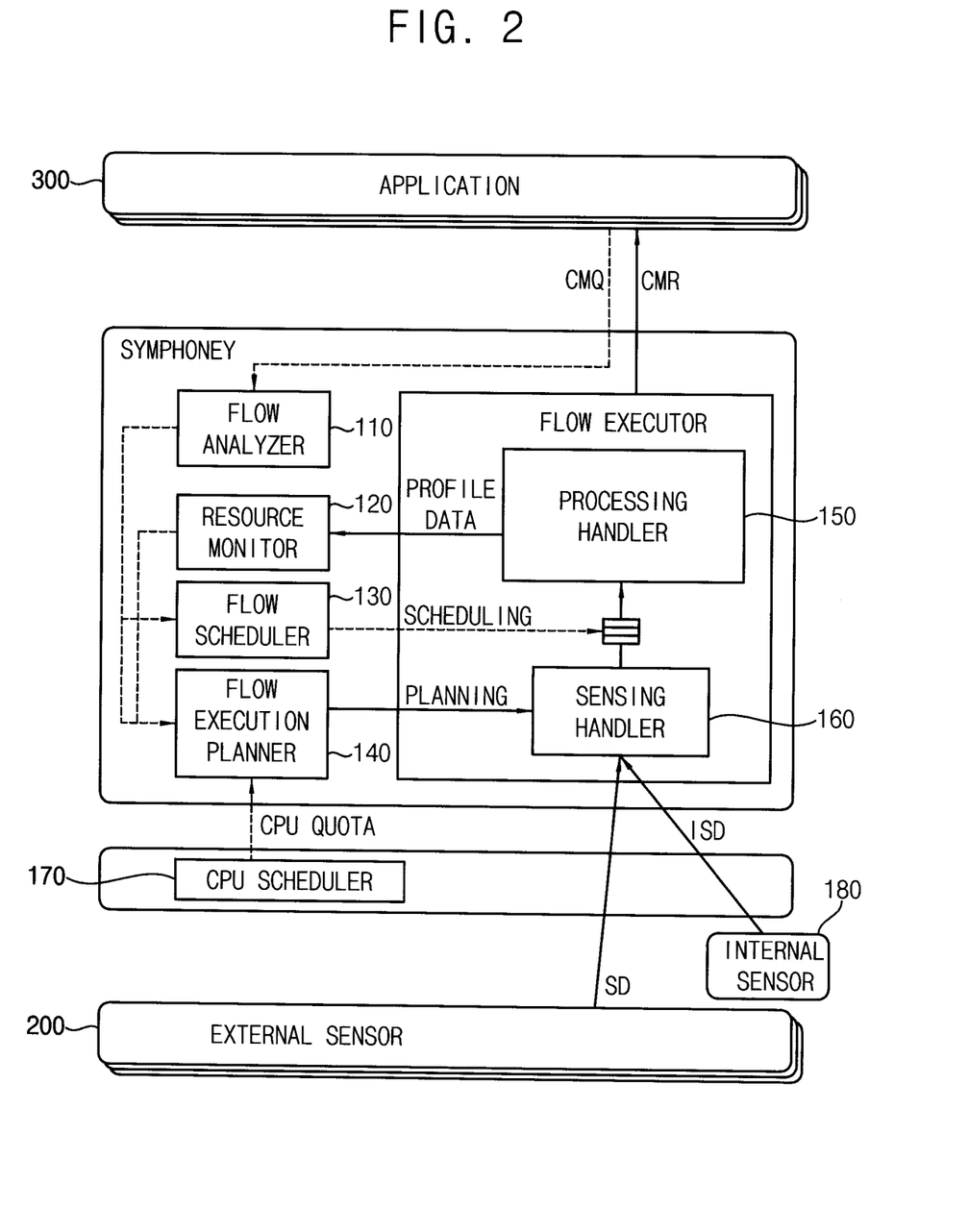
FIG. 2 is a detailed block diagram illustrating the context monitoring system of FIG. 1.

FIG. 2 is a detailed block diagram illustrating the context monitoring system of FIG. 1.

Referring to FIGS. 1 and 2, the mobile apparatus 100 includes a flow analyzer 110, a resource monitor 120, a flow scheduler 130, a flow execution planner 140, a flow executor and a CPU scheduler 170. The flow executor includes a processing handler 150 and a sensing handler 160. The mobile apparatus may further include an internal sensor 180.

The flow analyzer 110 receives the context monitoring request CMQ from the context monitoring application 300. The context monitoring request CMQ may include sensing flow information and an execution requirement.

The sensing flow information represents a flow of the sensing information which the context monitoring application 300 demands. The sensing flow information may correspond to a data flow graph shown in FIGS. 3A to 3C.

For example, the sensing flow information may be a data flow programming model of an XML interface. The sensing flow information of the XML interface may include an operator and an edge between the operators. The operator represents a unit of computation or I/O. The edge represents data dependencies between the operators.

The execution requirement includes a necessary monitoring interval and a monitoring delay.

The necessary monitoring interval represents how often the application 300 needs to monitor the user's situation. For example, CalorieMon application may require capturing the user's physical activity every several seconds to compute the total calorie expenditure of a day. Typically, the shorter the interval is, the higher the utility of the application is. Applications 300 specify the preferred monitoring interval tied with utility values for each interval, which is expressed as a utility function. The mobile apparatus 100 may coordinate the resource uses to maximize the utility of the context monitoring applications 300.

The monitoring delay represents a maximum tolerable delay of the context monitoring applications 300. The delay means the time to deliver final context monitoring results CMR to the application 300 from the moment of sensing.

In addition, the execution requirement may further include an accuracy of the context monitoring result CMR.

The flow analyzer 110 determines a frame structure based on the sensing flow. The flow analyzer 110 may determine a size of C-FRAME and a size of F-FRAME based on the sensing flow. The flow analyzer 110 outputs the size of the C-FRAME and the size of the F-FRAME to the flow execution planner 140.

Generally, the sensed data stream is generated as a flat sequence of data. However, taken by the application 300, the sensed data stream is interpreted with a tailored structure. The application 300 extracts and determines a specific context from the sensed data stream. Knowledge on the frame structure of the sensed data stream gives useful hints in executing the application 300 and planning the resource use of the application 300, especially when a system deal with multiple concurrent applications under a resource contentious circumstance.

When an application A takes a sensed data stream S as input, a virtual structure of S may be extracted by inspecting the flow of A. The process of externalizing the virtual structure of S with respect to A is called as framing or frame externalization. The resulting structural entity of S is called as a frame. The sensed data stream may be framed differently by different applications 300. Also, the sensed data stream may be framed differently even for the same application 300.

The C-FRAME represents a context-frame. The C-FRAME means a sequence of the sensed data to produce the context monitoring result CMR. The mobile apparatus 100 uses the C-FRAME as a basic unit of data processing and resource allocation.

The F-FRAME represents a feature-frame. The F-FRAME means a sequence of the sensed data to execute a feature extraction operation. The C-FRAME includes a plurality of the F-FRAMEs.

Figure 4:
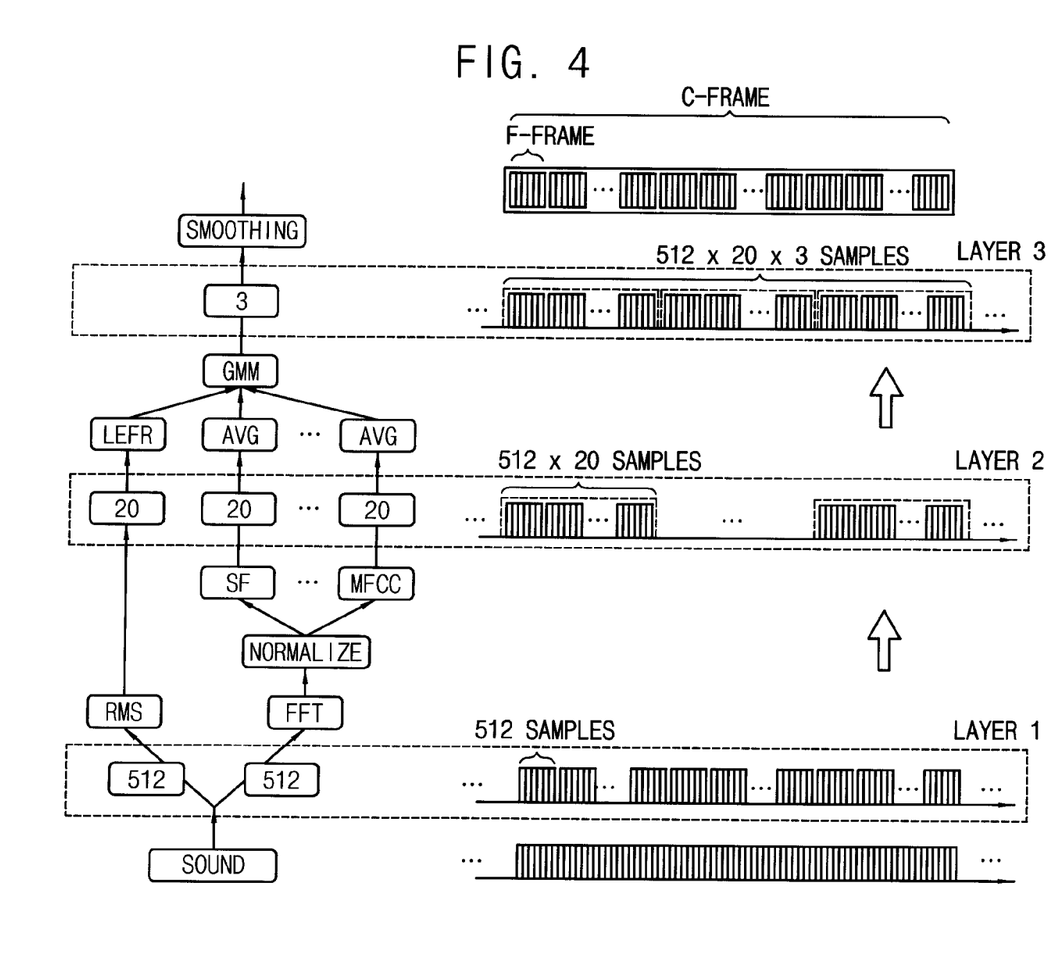
FIG. 4 is a conceptual diagram illustrating frame externalization of a sensed data stream executed by the mobile apparatus of FIG. 1.

Framing the sensed data stream is explained referring to FIG. 4 in detail.

The flow analyzer 110 outputs the monitoring delay of the execution requirement to the flow scheduler 130. The flow analyzer 110 outputs the necessary monitoring interval of the execution requirement to the flow execution planner 140. For example, the necessary monitoring interval may have a type of a utility function representing utility values according to the monitoring intervals.

The resource monitor 120 receives profile data from the flow executor. The profile data may include a CPU usage and an energy usage of the mobile apparatus 100. The CPU usage and the energy usage may be changed in real time according to other applications. The profile data may include a CPU usage and an energy usage of the processing handler 150 and the sensing handler 160.

The resource monitor 120 outputs the CPU usage and the energy usage to the flow execution planner 140.

For example, the CPU usage may be determined using an elapsed time for the C-FRAME execution, the time between the start and end of the C-FRAME execution.

For example, the energy usage may be determined using an offline profiling method. In the offline profiling method, the energy profiles for sensors, CPU and network interfaces which are major hardware components used by the sensing application 300 are prebuilt. The energy usage of the C-FRAME is estimated by adding the energy consumed to perform the operations to collect and process the C-FRAME based on the energy profiles.

The flow scheduler 130 receives the monitoring delay from the flow analyzer 110. The flow scheduler 130 determines an execution order of the F-FRAMEs of the sensing handler 160 based on the monitoring delay.

Figure 8:
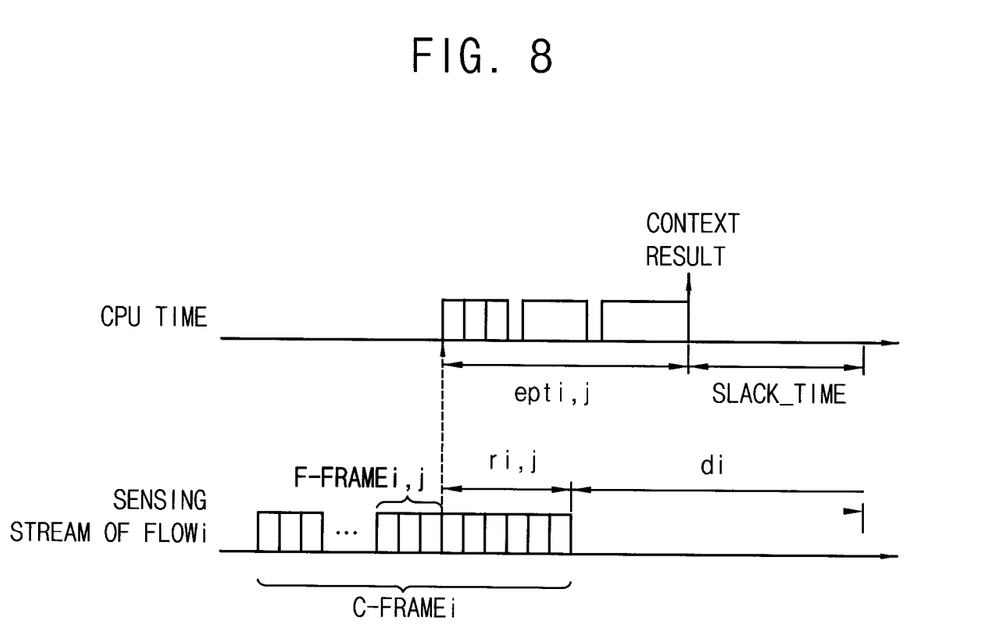
FIG. 8 is a conceptual diagram illustrating slack time estimation of F-FRAME executed by a flow scheduler of FIG. 2.

A method of determining the execution order of the F-FRAMEs by the flow scheduler 130 is explained referring to FIG. 8.

The flow execution planner 140 receives the size of the C-FRAME, the size of the F-FRAME and the necessary monitoring interval from the flow analyzer 110. The flow execution planner 140 receives the CPU usage and the energy usage from the resource monitor 120. The flow execution planner 140 may further receive a CPU quota allowing the execution of the sensing application 300 from the CPU scheduler 170.

The flow execution planner 140 controls the sensing flow of the sensing handler 160 using the size of the C-FRAME, the size of the F-FRAME and the necessary monitoring interval.

The flow execution planner 140 determines a monitoring interval of a sensing operator of the sensing handler 160 using the size of the C-FRAME, the size of the F-FRAME and the necessary monitoring interval. A skip time may be determined by the size of the C-FRAME and the monitoring interval. The sensing handler 160 senses the data corresponding to the size of the C-FRAME, and stops sensing the data during the skip time. The sensing handler 160 repeats the sensing and the suspension in a cycle of the monitoring interval.

When the sensing handler 160 includes a plurality of the sensing operators, the flow execution planner 140 may determine the monitoring interval for each sensing operator.

The flow execution planner 140 may control the sensing flow of the sensing handler 160 using the size of the C-FRAME, the size of the F-FRAME, the necessary monitoring interval, the CPU usage and the energy usage. The flow execution planner 140 may control the sensing flow of the sensing handler 160 further using the CPU quota. The CPU quota means a limit of a CPU usage allowed to the context monitoring application 300. The CPU quota may be set by an operating system (OS) or set by the user.

When the concurrent sensing flows are FLOWi and the monitoring intervals of the C-FRAMEs are pi, the flow execution planner 140 determines the monitoring interval pi of the C-FRAME using following Formulas 1 to 3.

$$\text{maximize} \Sigma ui(pi) \qquad \text{[Formula 1]}$$

$$\Sigma cti/pi \leq 1-CPUf \qquad \text{[Formula 2]}$$

$$\Sigma eci/pi \leq Elimit \qquad \text{[Formula 3]}$$

In Formula 1, ui means a utility function of the FLOWi. The utility function represents a utility value of the application according to the monitoring interval pi. The flow execution planner 140 determines the monitoring interval pi to maximize the utility of the plurality of the sensing flows.

In Formula 2, cti means a CPU time required to process the C-FRAME of FLOWi. CPUf means the CPU portion taken by other applications. 1−CPUf means the CPU availability for the sensing applications. Alternatively, the CPU availability may be set by the user regardless of the CPUf which means the CPU portion taken by other applications. The flow execution planner 140 determines the monitoring interval pi under the constraints of Formula 2.

In Formula 3, eci means energy required to process the C-FRAME of FLOWi. Elimit means an energy availability for the sensing applications. The flow execution planner 140 determines the monitoring interval pi under the constraints of Formula 3.

The CPU usage may be determined using eti which means elapsed time for the C-FRAME execution of FLOWi, the time between the start and end of the C-FRAME execution. Using the elapsed time eti, cti in Formula 2 may be approximated as eti*(1−CPUf). Accordingly, Formula 2 may be represented as following Formula 4.

$$\Sigma eti/pi \leq 1 \qquad \text{[Formula 4]}$$

Figure 5A:
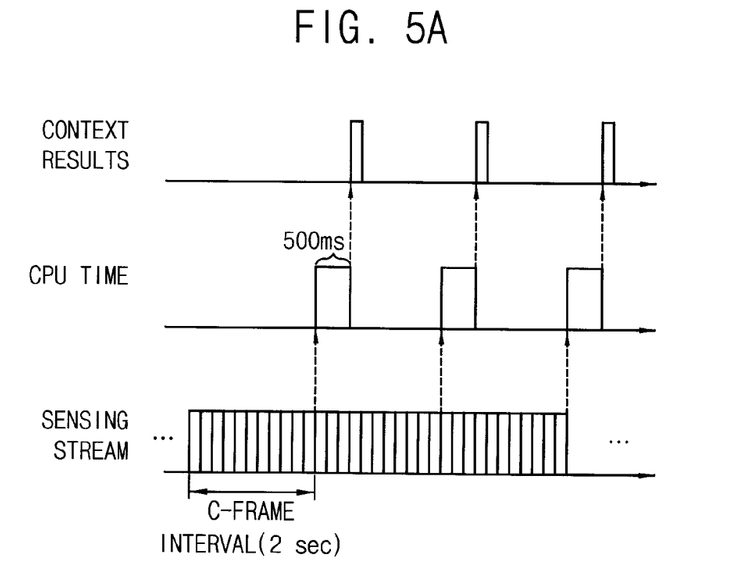
FIGS. 5A and 5B are conceptual diagrams illustrating C-FRAME based resource allocation executed by the mobile apparatus of FIG. 1.
Figure 5B:
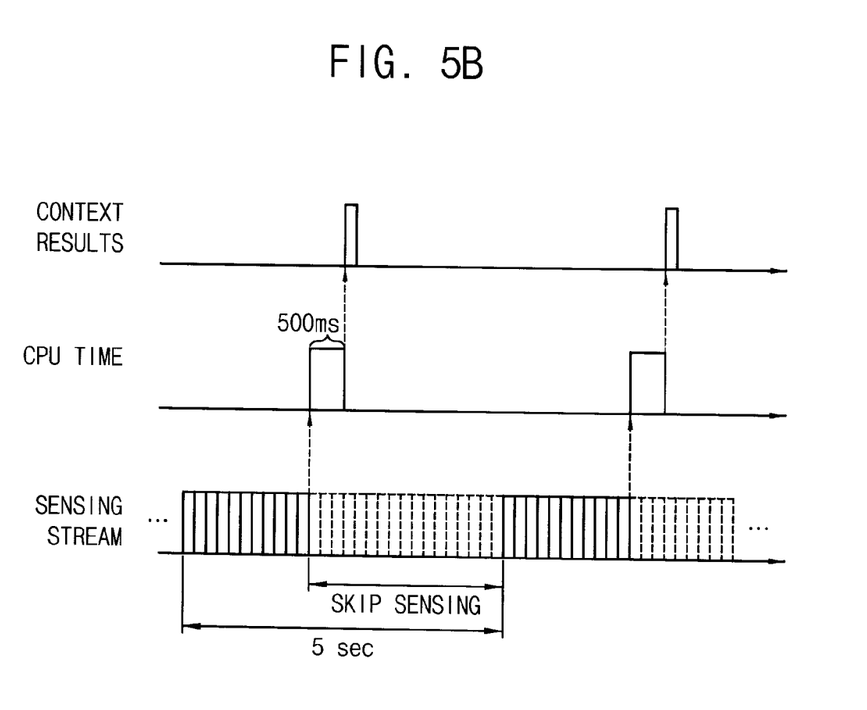
Figure 6:
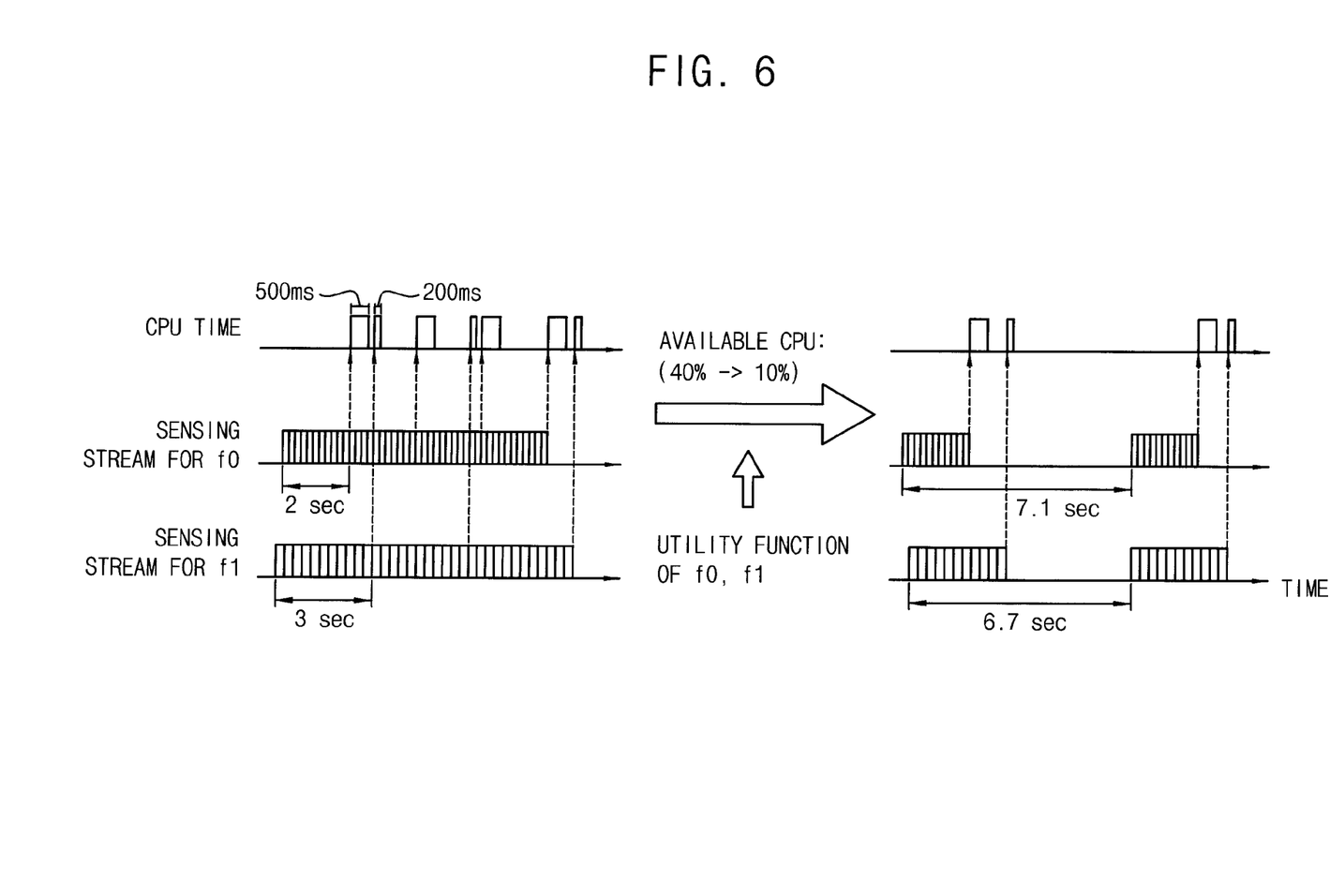
FIG. 6 is a conceptual diagram illustrating C-FRAME based flow coordination executed by the mobile apparatus of FIG. 1.

A specific operation of the flow execution planner 140 may be explained referring to FIGS. 5 and 6 in detail.

The processing handler 150 includes a plurality of processing operators. The processing handler 150 controls an operation of the processing operator. The processing handler 150 controls an operation of the processing operator according to scheduling of the flow scheduler 130. The processing operators may be operated in a unit of the F-FRAME.

The sensing handler 160 includes a plurality of sensing operators. The sensing handler 160 controls an operation of the sensing operator according to planning of the flow execution planner 140. The sensing operators receive the monitoring interval information. The sensing operators sense the data in a unit of C-FRAME and stop sensing during the skip time based on the monitoring interval information.

Figure 7:
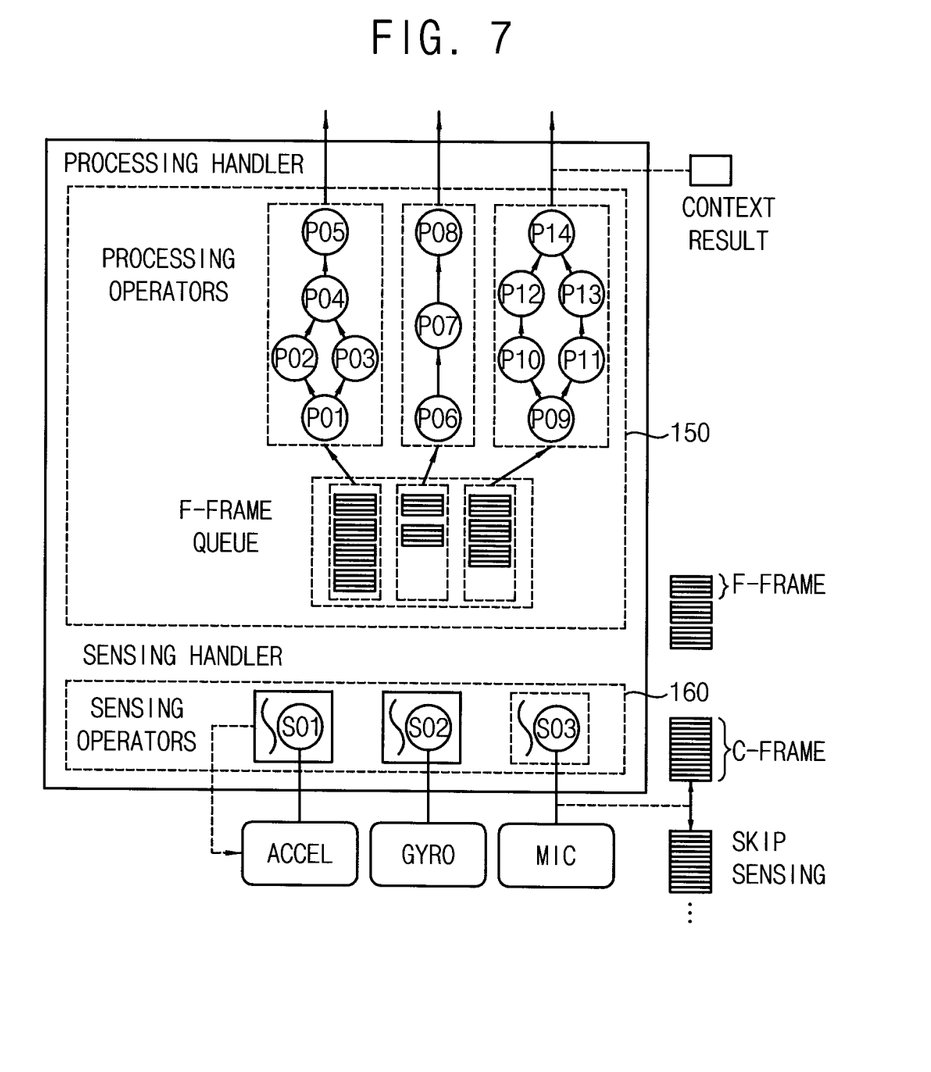
FIG. 7 is a conceptual diagram illustrating an operation of a flow executor of FIG. 2.

The operations of the processing handler 150 and the sensing handler 160 are explained referring to FIG. 7 in detail.

The CPU scheduler 170 outputs the CPU quota to the flow execution planner 140. The CPU scheduler 170 may be included in the operating system.

The internal sensor 180 outputs internal sensed data ISD to the sensing operator of the sensing handler 160. Alternatively, the internal sensor 180 may output feature data extracted from the internal sensed data ISD to the sensing operator.

For example, the internal sensor 180 may include a plurality of internal sensors. The internal sensor 180 may be a light sensor, a temperature sensor, a position sensor, a dust sensor, an ultraviolet ray sensor, a hygrometer, a carbon dioxide detector, an ambient sound detector, an accelerometer and so on. Accordingly, the internal sensor 180 may detect light, temperature, position, dust quantity, ultraviolet ray quantity, humidity, carbon dioxide quantity, ambient sound, acceleration and so on.

The internal sensed data ISD from the internal sensor 180 are provided to the sensing handler 160, and are used to determine whether the internal sensed data ISD satisfies a context requested by the context monitoring application 300.

Figure 3A:
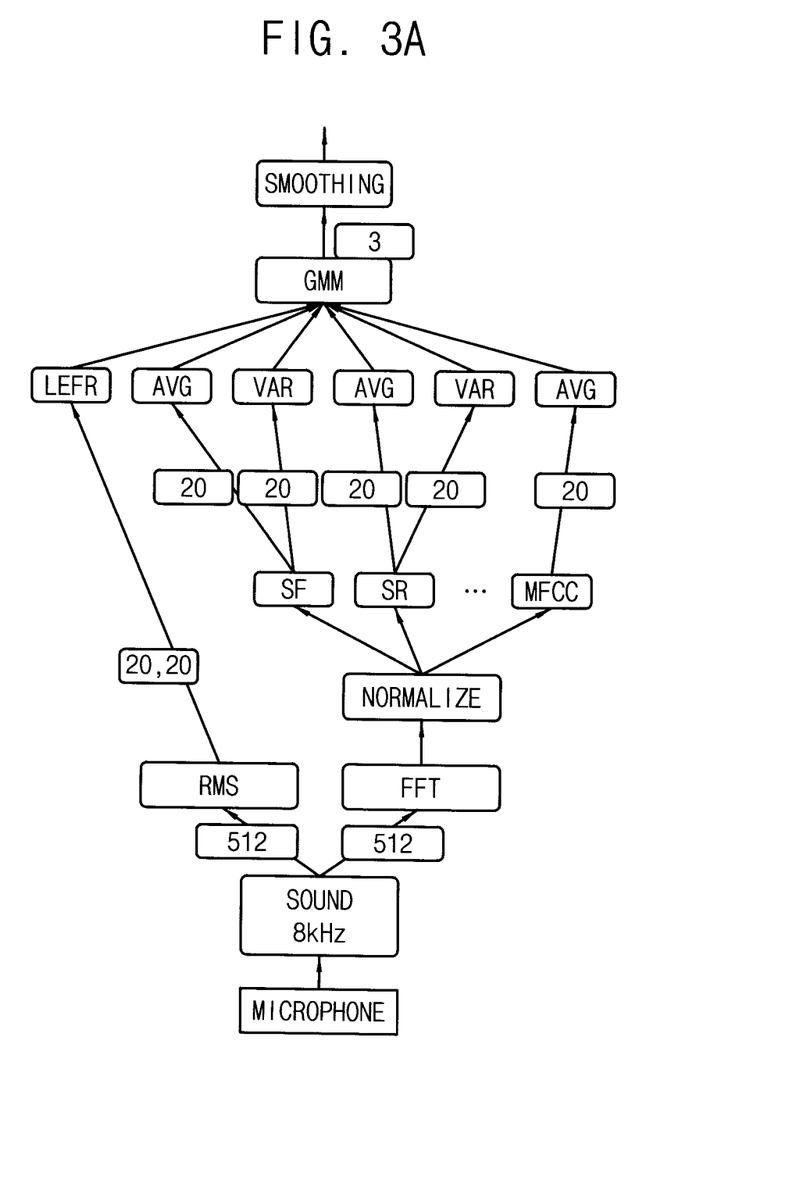
FIG. 3A is a conceptual diagram illustrating a sensing flow of a first context monitoring application executed by the mobile apparatus of FIG. 1.
Figure 3B:
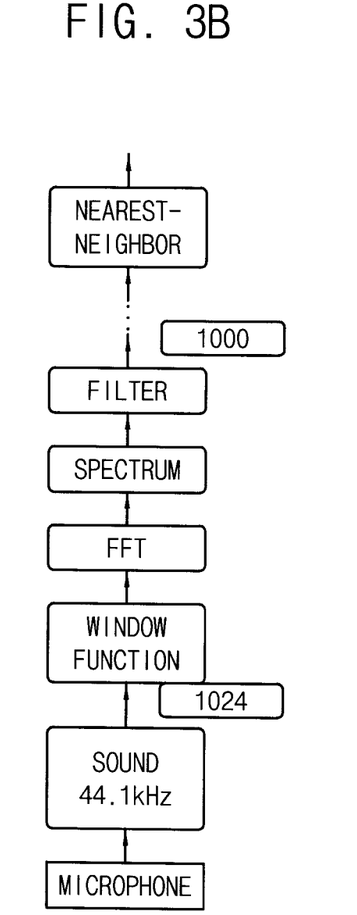
FIG. 3B is a conceptual diagram illustrating a sensing flow of a second context monitoring application executed by the mobile apparatus of FIG. 1.
Figure 3C:
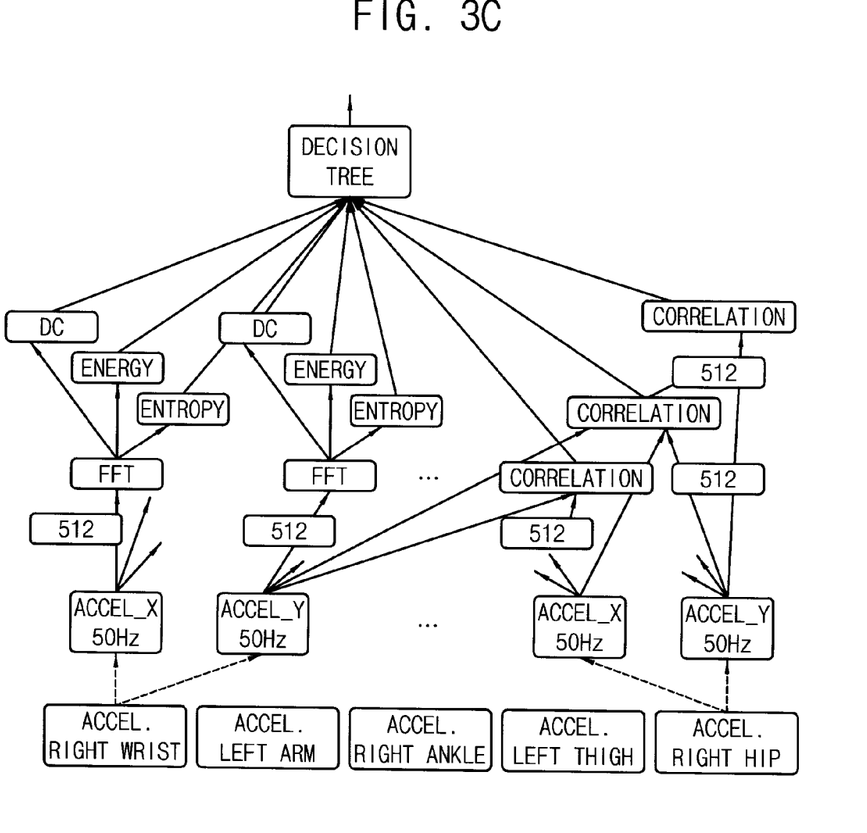
FIG. 3C is a conceptual diagram illustrating a sensing flow of a third context monitoring application executed by the mobile apparatus of FIG. 1.

FIG. 3A is a conceptual diagram illustrating a sensing flow of a first context monitoring application executed by the mobile apparatus 100 of FIG. 1. FIG. 3B is a conceptual diagram illustrating a sensing flow of a second context monitoring application executed by the mobile apparatus 100 of FIG. 1. FIG. 3C is a conceptual diagram illustrating a sensing flow of a third context monitoring application executed by the mobile apparatus 100 of FIG. 1.

In FIGS. 3A to 3C, a rectangular box in a lowermost level represents an external sensor or an internal sensor. Chamfered rectangular boxes represent sensing operators and processing operators. Numbers between the operators represent window sizes of sensed data streams.

Referring to FIGS. 3A, 3B and 3C, FIG. 3A represents a sensing flow of a context monitoring application, ChildMon. ChildMon allows working parents to be aware of realtime activities of their kindergarten child during classes and filedtrips. Childmon monitors children's activities like talking and playing using a backpack-attached mobile apparatus and notifies the parents of the distinguished activities. Childmon senses sound data to determine the children's activities.

In FIG. 3A, the sensing operator, SOUND, continuously samples audio data at 8 kHz. The audio data is transmitted two processing operators RMS and FFT which are connected to SOUND. Results of RMS and FFT are further processed through a series of operators and transmitted to GMM (Gaussian Mixture Model) and SMOOTHING. The children's activity is determined by SMOOTHING FIG. 3B represents a sensing flow of a context monitoring application, IndoorNavi. IndoorNavi helps a mobile user to navigate large-scale building complexes. For the navigation, the application continuously localizes a location of the mobile apparatus.

In FIG. 3B, the sensing operator, SOUND, continuously generates sound data at 44.1 kHz and transmits the sound data to a processing operator, WINDOW FUNCTION next to SOUND. A result of WINDOW FUNCTION is transmitted to NEAREST-NEIGHBOR through a series of operators.

FIG. 3C represents a sensing flow of a context monitoring application, CalorieMon. CalorieMon monitors a user's physical activities during daily exercise and estimates realtime caloric expenditure of the user. The application utilizes a plurality of accelerometers disposed in different body portions.

In FIG. 3C, the sensing operators, ACCEL_X and ACCEL_Y, continuously samples acceleration data at 50 Hz and transmits the acceleration data to a processing operator, FFT, CORRELATION connected to ACCEL_X and ACCEL_Y. Results of FFT, CORRELATION are transmitted to DECISION TREE through a series of operators. By DECISION TREE, the caloric expenditure of the user is calculated.

FIG. 4 is a conceptual diagram illustrating frame externalization of a sensed data stream executed by the mobile apparatus of FIG. 1.

FIG. 4 represents that ChildMon frames the sound stream into the C-FRAME and the F-FRAME.

Referring to FIGS. 1 to 4, the flow analyzer 110 may determine a size of the C-FRAME and a size of the F-FRAME based on the sensing flow of ChildMon.

In FIG. 4, the sound stream of 8 kHz is framed by ChildMon in three layers. In a first layer, a sequence of 512 consecutive samples is framed for feature extraction. In a second layer, 20 of the first layer frames are combined for classification. In a third layer, 3 of the second layer frames are combined to generate a final context monitoring result. Therefore, 512*20*3 samples generate the final context monitoring result. Herein, the size of the F-FRAME is 512 samples. The size of the C-FRAME is 512*20*3 samples.

FIGS. 5A and 5B are conceptual diagrams illustrating C-FRAME based resource allocation executed by the mobile apparatus 100 of FIG. 1. FIG. 6 is a conceptual diagram illustrating C-FRAME based flow coordination executed by the mobile apparatus 100 of FIG. 1.

Referring to FIGS. 1 to 6, the C-FRAME is the basic unit of data processing and resource allocation. Collecting the C-FRAME and performing subsequent operations can hardly be ceased in the middle, in order to generate an accurate and timely context result. On the other hand, it is often tolerable to temporarily pause the whole operations once the C-FRAME is completely processed.

Accordingly, 'collecting and processing the C-FRAME' is a unit of resource allocation. Each C-FRAME is allocated with the right and deserved amount of resources to collect and process the C-FRAME. A flow is coordinated by assigning a monitoring interval of the C-FRAME. The monitoring interval of the C-FRAME may be set to guarantee the processing of the C-FRAME in each interval with the given resource availability.

In FIG. 5A, the CPU availability of the mobile apparatus is 40%. A length of the C-FRAME is 2 sec. A CPU time to process the C-FRAME is 500 ms. Thus, the maximum CPU usage of the C-FRAME is 500 ms/2 sec, 25%.

The CPU availability (40%) is greater than the maximum CPU usage (25%) of the C-FRAME so that the monitoring interval of the C-FRAME may be set to 2 sec. In FIG. 5A, the skip time when the sensing operator stops sensing the data does not exist. Thus, the sensing operator continuously senses the data.

In FIG. 5B, the CPU availability of the mobile apparatus is 10%. A length of the C-FRAME is 2 sec. A CPU time to process the C-FRAME is 500 ms. Thus, the maximum CPU usage of the C-FRAME is 500 ms/2 sec, 25%.

The CPU availability (10%) is less than the maximum CPU usage (25%) of the C-FRAME so that the C-FRAME may not use the maximum CPU usage but the C-FRAME may use the CPU usage equal to or less than 10%. Therefore, the monitoring interval of the C-FRAME may be set to 5 sec. The CPU usage of the C-FRAME is 500 ms/5 sec, 10%.

In FIG. 5B, the sensing time of the sensing operator is 2 sec and the skip time when the sensing operator stops sensing the data is 3 sec. Thus, the sensing operator repeatedly senses the data and stops sensing the data in a cycle of 5 sec.

For multiple concurrent flows, the coordination may be performed to assign different monitoring intervals of the C-FRAME for the different flows. The flows may be coordinated to maximize the total utility of corresponding applications under the given resource availability.

In FIG. 6, when the CPU availability is 40%, the sensing stream of a flow f0 which has the C-FRAME having the length of 2 sec is sensed in the monitoring interval of 2 sec. The CPU usage of the flow f0 is 500 ms/2 sec, 25%. The sensing stream of a flow f1 which has the C-FRAME having the length of 3 sec is sensed in the monitoring interval of 3 sec. The CPU usage of the flow f0 is 200 ms/3 sec, about 6.67%. A sum of the CPU usage of the flow f1) and the CPU usage of the flow f1 is less than the CPU availability 40% so that the flow f1) and the flow f1 maximally uses the CPU without the skip time.

When the CPU availability is changed to 10% from 40%, the CPU usages of the flow f0 and the flow f1 are adjusted. The CPU usages of the flow f0 and the flow f1 may be determined using the utility function of the flow f0 and the utility function of the flow f1. The flow execution planner 140 may determine the monitoring interval of the C-FRAME of the flow f0 and the monitoring interval of the C-FRAME of the flow f1 to maximize the utility of the flow f0 and the utility of the flow f1 under the given resource constraints. For example, the monitoring interval of the C-FRAME of the flow f0 may be set to about 7.1 sec. The skip time of the flow f0 may be about 5.1 sec. The CPU usage of the flow f0 is about 500 ms/7.1 sec, about 7.0%. For example, the monitoring interval of the C-FRAME of the flow f1 may be set to about 6.7 sec. The skip time of the flow f1 may be about 4.7 sec. The CPU usage of the flow f1 is about 200 ms/6.7 sec, about 3.0%.

As explained above, the actual execution of the flow in the mobile apparatus 100 is executed in the unit of the F-FRAME while the allocation is executed for each C-FRAME. Thus, the flexibility in the scheduling of the flow execution may be obtained. For example, the size of the single C-FRAME may be large (e.g. about 4 MB with IndoorNavi). Accordingly, processing the whole c-frame in a single step may cause sudden CPU usage peaks and induce quite a long delay. According to the present exemplary embodiment, the flow is processed in the unit of smaller-size F-FRAMES so that the mobile apparatus 100 flexibly schedule concurrent applications in order to meet the delay requirements under contentious situation.

FIG. 7 is a conceptual diagram illustrating an operation of the flow executor of FIG. 2.

Referring to FIGS. 1 to 7, the mobile system includes sensors such as an accelerometer Accel, a gyroscope Gyro and a microphone Mic.

The sensing handler 160 includes a first sensing operator S01 operating a sensing stream of the accelerometer Accel, a second sensing operator S02 operating a sensing stream of the gyroscope Gyro and a third sensing operator S03 operating a sensing stream of the microphone Mic.

The first to third sensing operators S01, S02 and S03 continuously sense the data during sensing times corresponding to respective lengths of the C-FRAMEs and stop sensing during skip times which are determined by subtracting the sensing times from the monitoring intervals. The first to third sensing operators S01, S02 and S03 may have different sizes of the C-FRAMEs. The first to third sensing operators S01, S02 and S03 may have different monitoring intervals of the C-FRAMEs.

The sensing handler 160 manages the sensing operators each of which runs in a separate thread. The first sensing operator S01 stores acceleration sensing streams to a first F-FRAME queue in a unit of the F-FRAME. The second sensing operator S02 stores gyro sensing streams to a second F-FRAME queue in a unit of the F-FRAME. The third sensing operator S03 stores sound sensing streams to a third F-FRAME queue in a unit of the F-FRAME. The first to third sensing operators S01, S02 and S03 may have different sizes of the F-FRAME.

The processing handler 150 controls the execution of the subsequent processing operators. When the flow scheduler 130 picks one of the flows, the processing handler 150 takes the F-FRAME from the flow's F-FRAME queue and processes the F-FRAME using the processing operator. For example, when the flow scheduler 130 selects a first flow, the processing handler 150 takes the acceleration F-FRAME from the first F-FRAME queue and processes the acceleration F-FRAME using the processing operators P01 to P05. For example, when the flow scheduler 130 selects a second flow, the processing handler 150 takes the gyro F-FRAME from the second F-FRAME queue and processes the gyro F-FRAME using the processing operators P06 to P08. For example, when the flow scheduler 130 selects a third flow, the processing handler 150 takes the sound F-FRAME from the third F-FRAME queue and processes the sound F-FRAME using the processing operators P09 to P14.

FIG. 8 is a conceptual diagram illustrating slack time estimation of F-FRAME executed by the flow scheduler 130 of FIG. 2.

Referring to FIGS. 1 to 8, the flow scheduler 130 determines the execution order of the F-FRAMEs piled up in the F-FRAME queues. For example, the flow scheduler 130 determines the execution order of the F-FRAMEs using following Formula 5.

$$\text{maximize} \Sigma \text{satisfy}(ci) \qquad \text{[Formula 5]}$$

$ci$ means a context monitoring result for FLOWi generated by processing the F-FRAMEs in the F-FRAME queue. The function of satisfy(ci) is a binary function to evaluate if $ci$ is generated within a tolerable delay; satisfy(ci) is 1 if the delay of $ci$ is less than the tolerable delay and 0, otherwise. The tolerable delay is defined as the time taken to generate the context monitoring result from the moment that the final F-FRAME in the C-FRAME is ready.

The flow scheduler 130 may determine the execution order of the F-FRAMEs to obtain the maximum number of the context monitoring results by processing the F-FRAMEs in the tolerable delay.

In the present exemplary embodiment, the flow scheduler 130 may adopt a least slack time method. The flow scheduler 130 calculates slack times for all F-FRAMEs in the F-FRAME queue. The flow scheduler 130 controls the processing handler 150 to process the F-FRAME having the least slack time among the F-FRAMEs.

F-FRAME$i,j$ means j-th F-FRAME of i-th C-FRAME (C-FRAME$i$). The slack time of the F-FRAME$i,j$ may be calculated by subtracting the processing time of remaining F-FRAMEs in the C-FRAME$i$ from a delivery deadline. The slack time of the F-FRAME$i,j$ may be represented as following Formula 6.

$$\text{slacktime}(F\text{-FRAME}i,j) = di + ri,j - epti,j \qquad \text{[Formula 6]}$$

$di$ is the tolerable delay of the FLOWi. $ri,j$ is the remaining time to collect the whole C-FRAME with upcoming F-FRAMEs. $epti,j$ is the expected time to process the unprocessed F-FRAMEs in the C-FRAME$i$. The unprocessed F-FRAMEs are from F-FRAME$i,j$ to the final F-FRAME in the C-FRAME$i$.

The flow scheduler 130 may $ri,j$ using a position of the F-FRAME$i,j$ in the C-FRAME$i$ and the number of the remaining F-FRAMEs and a sampling rate. The flow scheduler 130 continuously profiles processing times of the F-FRAMES and estimates $epti,j$ from the profiling results for the F-FRAMEs of the previous C-FRAME.

According to the present inventive concept as explained above, the sensing operators collect the sensed data in the unit of the C-FRAME and the processing operators executes the sensing flow in the unit of the F-FRAME so that resource usages of the concurrent applications may be adjusted. Thus the utility of the applications may be improved.

The flow execution planner 140 adjusts the monitoring interval of the sensing operators of the sensing handler 160 so that collecting the sensed data between the sensing operators may be properly controlled.

The flow scheduler 130 may properly adjust the execution order of the F-FRAMEs of the plurality of flows.

The foregoing is illustrative of the present inventive concept and is not to be construed as limiting thereof. Although a few example embodiments of the present inventive concept have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of the present inventive concept and is not to be construed as limited to the specific example embodiments disclosed, and that modifications to the disclosed example embodiments, as well as other example embodiments, are intended to be included within the scope of the appended claims. The present inventive concept is defined by the following claims, with equivalents of the claims to be included therein.

What is claimed is:

1. A mobile apparatus comprising a non-transitory processor-readable medium storing instructions for:
    sensing data during a sensing time corresponding to a size of C-FRAME and stopping sensing during a skip time using a sensing operator, a sensing handler including a plurality of the sensing operators, the C-FRAME being a sequence of the sensed data to produce a context monitoring result from the sequence of the sensed data; and
    executing the sensed data of the sensing operator in a unit of F-FRAME using a processing operator, a processing handler including a plurality of the processing operators, the F-FRAME being a sequence of the sensed data to a feature from the sequence of the sensed data,
    wherein the context monitoring result is produced from a plurality of the features, and
    the size of the C-FRAME is greater than a size of the F-FRAME.

2. The mobile apparatus of claim 1, wherein the C-FRAME includes a plurality of the F-FRAMEs.

3. The mobile apparatus of claim 1, further comprising a flow analyzer receiving information for a sensing flow from an application and determining a size of the C-FRAME of the sensing flow and a size of the F-FRAME of the sensing flow.

4. The mobile apparatus of claim 3, wherein the flow analyzer receives a necessary monitoring interval and a monitoring delay from the application, the necessary monitoring interval representing how often the application needs to monitor a user's situation, the monitoring delay representing time taken to generate the context monitoring result from a moment that a final F-FRAME in the C-FRAME is ready.

5. The mobile apparatus of claim 4, further comprising a flow execution planner determining a monitoring interval of the C-FRAME based on the size of the C-FRAME, the size of the F-FRAME and the necessary monitoring interval and outputting the monitoring interval of the C-FRAME to the sensing handler,
wherein the monitoring interval of the C-FRAME of the sensing flow is substantially equal to a sum of the sensing time and the skip time.

6. The mobile apparatus of claim 5, further comprising a resource monitor determining a CPU availability of the mobile apparatus and outputting the CPU availability to the flow execution planner,
wherein the flow execution planner determines the monitoring interval of the C-FRAME of the sensing flow based on the size of the C-FRAME, the size of the F-FRAME, the necessary monitoring interval and the CPU availability.

7. The mobile apparatus of claim 5, wherein the necessary monitoring interval has a type of utility function, the utility function having utility values of the application according to the monitoring intervals.

8. The mobile apparatus of claim 7, wherein when the monitoring interval of a plurality of sensing flows is pi and the utility function of the sensing flows is ui, the flow execution planner determines the monitoring interval as a formula, max imize$\Sigma ui(pi)$.

9. The mobile apparatus of claim 8, wherein when cti is a CPU time required to process the C-FRAME of a flow, FLOWi and 1−CPUf is a CPU availability for the applications, the flow execution planner determines the monitoring interval under a constraint of $\Sigma cti/pi \leq 1-CPUf$.

10. The mobile apparatus of claim 8, wherein when eci is energy required to process the C-FRAME of a flow, FLOWi and Elimit is an energy availability for the applications, the flow execution planner determines the monitoring interval under a constraint of $\Sigma eci/pi \leq E$ limit.

11. The mobile apparatus of claim 5, wherein the sensing flows include respective F-FRAME queues,
further comprising a flow scheduler determining an execution order of the F-FRAMEs by selecting a F-FRAME queue among the F-FRAME queues.

12. The mobile apparatus of claim 11, wherein the flow scheduler determines the execution order of the F-FRAMEs based on the monitoring delay.

13. The mobile apparatus of claim 12, wherein a function of satisfy(ci) represents 1 if a context monitoring result for i-th flow, FLOWi is generated by processing the F-FRAMEs in the F-FRAME queue in the monitoring delay and represents 0, otherwise, and
the flow scheduler determines the execution order of the F-FRAMEs using a formula, max imize$\Sigma$satisfy(ci).

14. The mobile apparatus of claim 13, wherein a j-th F-FRAME of an i-th C-FRAME (C-FRAMEi) is F-FRAMEi,j, di is a tolerable delay of the FLOWi, ri,j is a remaining time to collect the remaining F-FRAMEs in the C-FRAMEi, epti,j is an expected time to process the unprocessed F-FRAMEs in the C-FRAMEi and a slack time of the F-FRAMEi,j is determined as a formula, slacktime(F−FRAMEi, j)=di+ri, j−epti, j, and
the flow scheduler selects the F-FRAME having a least slack time.

15. The mobile apparatus of claim 1, further comprising a CPU scheduler outputting a CPU quota to the flow execution planner.

16. A method of executing a sensing flow, the method comprising:
sensing data during a sensing time corresponding to a size of C-FRAME and stopping sensing during a skip time using a plurality of sensing operators, the C-FRAME being a sequence of the sensed data to produce a context monitoring result from the sequence of the sensed data; and
executing the sensed data of the sensing operator in a unit of F-FRAME using a processing operator, the F-FRAME being a sequence of the sensed data to extract a feature from the sequence of the sensed data, wherein the context monitoring result is produced from a plurality of the features, and the size of the C-FRAME is greater than a size of the F-FRAME.

17. The method of claim 16, wherein the C-FRAME includes a plurality of the F-FRAMEs.

18. The method of claim 16, further comprising receiving information for a sensing flow from an application and determining a size of the C-FRAME of the sensing flow and a size of the F-FRAME of the sensing flow.

19. The method of claim 18, further comprising receiving a necessary monitoring interval and a monitoring delay from the application, the necessary monitoring interval representing how often the application needs to monitor a user's situation, the monitoring delay representing time taken to generate the context monitoring result from a moment that a final F-FRAME in the C-FRAME is ready.

20. The method of claim 19, further comprising determining a monitoring interval of the C-FRAME based on the size of the C-FRAME, the size of the F-FRAME and the necessary monitoring interval,
wherein the monitoring interval of the C-FRAME of the sensing flow is substantially equal to a sum of the sensing time and the skip time.

21. The method of claim 20, further comprising determining a CPU availability of the mobile apparatus,
wherein the monitoring interval of the C-FRAME of the sensing flow is determined based on the size of the C-FRAME, the size of the F-FRAME, the necessary monitoring interval and the CPU availability.

22. The method of claim 20, wherein the necessary monitoring interval has a type of utility function, the utility function having utility values of the application according to the monitoring intervals.

23. The method of claim 20, wherein the sensing flows include respective F-FRAME queues,
further comprising determining an execution order of the F-FRAMEs by selecting a F-FRAME queue among the F-FRAME queues.

24. The method of claim 23, wherein the execution order of the F-FRAMEs is determined based on the monitoring delay.

25. A method of monitoring a context, the method comprising:
receiving a context monitoring request from an application;
sensing data during a sensing time corresponding to a size of C-FRAME and stopping sensing during a skip time using a plurality of sensing operators based on the context monitoring request, the C-FRAME being a sequence of the sensed data to produce a context monitoring result from the sequence of the sensed data;
executing the sensed data of the sensing operator in a unit of F-FRAME using a processing operator based on the context monitoring request, the F-FRAME being a sequence of the sensed data to extract a feature from the sequence of the sensed data; and
outputting the context monitoring result to the application wherein the context monitoring result is produced from a plurality of the features, and the size of the C-FRAME is greater than a size of the F-FRAME.

26. A context monitoring system comprising:

a sensor generating sensed data;

a mobile apparatus comprising a non-transitory processor-readable medium storing instructions for:

sensing data during a sensing time corresponding to a size of C-FRAME and stopping sensing during a skip time using a sensing operator, a sensing handler including a plurality of the sensing operators, the C-FRAME being a sequence of the sensed data to produce a context monitoring result from the sequence of the sensed data; and a processing handler including a plurality of processing operators, the processing operator executing the sensed data of the sensing operator in a unit of F-FRAME using a processing operator, a processing handler including a plurality of the processing operators, the F-FRAME being a sequence of the sensed data to extract a feature from the sequence of the sensed data; and an application receiving the context monitoring result from the mobile apparatus, wherein the context monitoring result is produced from a plurality of the features, and the size of the C-FRAME is greater than a size of the F-FRAME.

* * * * *